United States Patent [19]

Kameyama et al.

[11] Patent Number: 5,151,499
[45] Date of Patent: Sep. 29, 1992

[54] PRODUCTION METHOD FOR PROTEIN-CONTAINING COMPOSITION

[75] Inventors: Shoju Kameyama; Kenmi Miyano; Motonori Hashimoto; Kazuo Takechi; Takao Ohmura; Yutaka Hirao; Yahiro Uemura; Kazumasa Yokoyama, all of Hirakata, Japan

[73] Assignee: The Green Cross Corporation, Osaka, Japan

[21] Appl. No.: 464,077

[22] Filed: Jan. 12, 1990

[30] Foreign Application Priority Data

Jan. 13, 1989 [JP] Japan ................................ 1-6736
Nov. 27, 1989 [JP] Japan ................................ 1-308466

[51] Int. Cl.⁵ .................... A61K 35/16; A61K 35/14; A61K 39/18; A61K 37/00
[52] U.S. Cl. .................................. 530/381; 530/380; 530/382; 530/383; 530/384; 530/386; 530/390.1
[58] Field of Search ............... 500/380, 383, 387, 386, 500/381, 382, 392, 384

[56] References Cited

U.S. PATENT DOCUMENTS

| | | | |
|---|---|---|---|
| 3,984,539 | 10/1976 | Khouw et al. | 530/387 |
| 4,296,027 | 10/1981 | Condie | 530/387 |
| 4,424,206 | 1/1984 | Ohmura et al. | 530/386 |
| 4,440,679 | 4/1984 | Fernandes et al. | 530/383 |
| 4,456,590 | 6/1984 | Rubinstein | 530/383 |
| 4,495,278 | 1/1985 | Thomas | 435/5 |
| 4,540,573 | 9/1985 | Neurath et al. | 530/383 X |
| 4,556,558 | 12/1985 | Rubinstein | 530/383 |
| 4,721,777 | 1/1988 | Uemura et al. | 530/387 |
| 4,764,369 | 8/1988 | Neurath et al. | 530/384 X |

FOREIGN PATENT DOCUMENTS

| | | |
|---|---|---|
| 131740 | 1/1985 | European Pat. Off. . |
| 8203871 | 11/1982 | PCT Int'l Appl. . |
| 2068002 | 8/1981 | United Kingdom . |

OTHER PUBLICATIONS

Merck Index, 10th Ed. 1983, pp. 110–111.
American Journal of Hematology, vol. 23, 1986, pp. 295–305.

Primary Examiner—Howard E. Schain
Attorney, Agent, or Firm—Sughrue, Mion, Zinn, Macpeak & Seas

[57] ABSTRACT

A method of producing a virus-inactivated protein-containing composition from a protein-containing composition which may be contaminated with virus. The method according to the present invention permits production of pharmaceutically safer virus-inactivated protein preparations without spoiling the protein activity.

16 Claims, 3 Drawing Sheets

PRODUCTION METHOD FOR PROTEIN-CONTAINING COMPOSITION

BACKGROUND OF THE INVENTION

The present invention relates to a method of producing a substantially-virus-inactivated protein-containing composition from a protein-containing composition which may be contaminated with virus.

There is a possibility that compositions containing human-blood-derived protein may be contaminated with viruses, e.g., hepatitis virus and AIDS virus.

There are some known methods in which a protein-containing liquid composition is heated to prevent transmission of these viruses (Unexamined Japanese Patent Application Laid Open Nos. 145615/1980 corresponding to U.S. Pat. No. 4,297,344 and EP Publication No. 18561; 139422/1981 corresponding to U.S. Pat. No. 4,440,679 and EP Publication No. 35204; and 106594/1981 corresponding to U.S. Pat. No. 4,361,652 and DE-3102217).

Also known is a method in which a protein-containing dry composition is heated [Published Japanese Translation of PCT Patent Application from Other Country (KOHYO) No. 500548/1983 corresponding to U.S. Pat. No. 4,495,278 and EP Publication No. 77355; and Unexamined Japanese Patent Application Laid Open No. 213721/1983 corresponding to U.S. Pat. No. 4,556,558 and EP Publication No. 171506.].

Another method is known in which a protein-containing composition is brought into contact with trialkyl phosphate to remove viruses (Unexamined Japanese Patent Application Laid Open No. 51116/1985 corresponding to U.S. Pat. No. 4,540,573 and EP Publication No. 131740).

However, highly heat resistant viruses may remain active through heat treatment and non-envelope viruses may remain active through trialkyl phosphate treatment.

Also, conventional methods have been faulty in that the protein activity decreases during trialkyl phosphate treatment.

The object of the present invention is to provide a method of efficiently inactivating contaminant viruses almost without spoiling the protein activity and thus producing a pharmaceutically safer protein-containing composition.

SUMMARY OF THE INVENTION

To solve these subjects, the present invention provides a production method for a virus-inactivated protein-containing composition comprising a process wherein a protein-containing liquid composition which may be contaminated with virus is brought into contact with trialkyl phosphate and a process wherein a dry protein-containing composition is heated.

The present invention also provides a production method for a virus-inactivated protein-containing composition characterized in that a protein-containing liquid composition which may be contaminated with virus is brought into contact with trialkyl phosphate in the presence of a protease inhibitor.

According to the present invention, a protein-containing composition wherein viruses were efficiently inactivated can be produced without spoiling the protein activity.

DETAILED DESCRIPTION OF THE INVENTION

Figure 1:
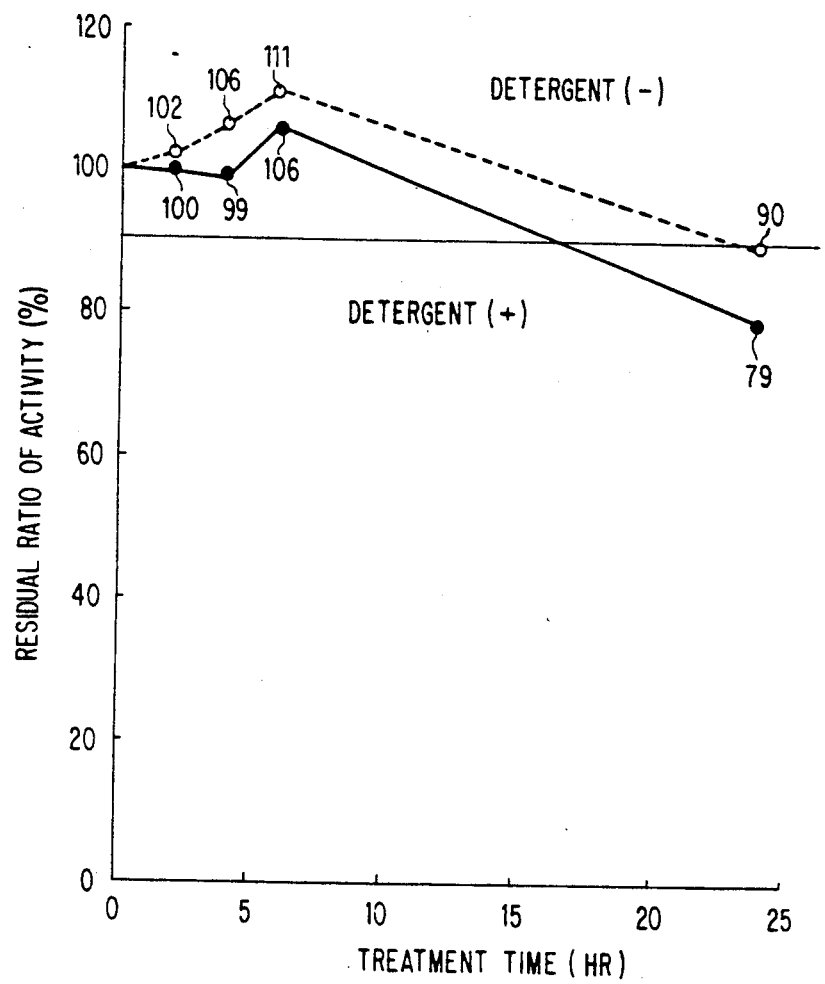
FIG. 1 shows time courses of the influence of surfactant treatment on the residual activity ratio of blood coagulation factor VIII: -○- represents data obtained in the absence of a surfactant; -●- represents data obtained in the presence of a surfactant.

There is no particular limitation posed on the protein to which the method of the present invention is applied. Examples of such protein include plasma-derived proteins, proteins derived from other tissues and proteins obtained by gene recombination or tissue culture. Specific examples of the protein include plasminogen, blood coagulation factor V, blood coagulation factor VII, blood coagulation factor VIII, blood coagulation factor IX, blood coagulation factor XIII, antithrombin III, haptoglobin, thrombin, prothrombin, immunoglobulin, fibrinogen, fibronectin, albumin, hemoglobin, interferon and plasminogen activator. The protein-containing liquid composition is not subject to particular limitation as long as it contains a protein as described above.

There is no particular limitation posed on the protein-containing liquid composition to which the method of the present invention is applied. Examples thereof include plasma or tissue extracts, solutions comprising a fraction obtained by treating a plasma or tissue extract by various fractionation methods, culture broths obtained by culturing a gene recombinant host or tissue and commercially available protein preparations (in a liquid form) or their solutions.

Also, the degree of purification of the protein-containing liquid composition of the present invention in contact with trialkyl phosphate is not subject to particular limitation; it is possible to apply the method of the present invention to any degree of purification. Therefore, the composition may be brought into contact with trialkyl phosphate at any step during protein separation and purification.

Although trialkyl phosphate treatment and heat treatment may precede or follow each other, it is preferable to conduct trialkyl phosphate treatment prior to the other.

The trialkyl phosphate used for the present invention is not subject to particular limitation, but it is preferable to use tri-(n-butyl) phosphate, tri-(tert-butyl) phosphate, tri-(n-hexyl) phosphate, tri-(2-ethylhexyl) phosphate, tri-(n-decyl) phosphate or the like. Tri-(n-butyl) phosphate (hereinafter referred to as TNBP) is especially preferable. It is also possible to use a mixture of two or more different trialkyl phosphates.

The trialkyl phosphate for the present invention is used in an amount between 0.01 to 10 (w/v) %, preferably about 0.1 to 3 (w/v) %.

Trialkyl phosphate may be used in the presence or absence of a surfactant. It is preferable to use trialkyl phosphate in combination with a surfactant. The surfactant may be added in any step before, simultaneously with, or after the contact of trialkyl phosphate with the protein-containing liquid composition. The surfactant functions to enhance the contact of the viruses in the protein-containing composition with trialkyl phosphate.

Examples of the surfactant include polyoxyethylene derivatives of fatty acid; partial esters of anhydrous sorbitol such as Polysorbate 80 (trade name: Tween 80, etc.) and Polysorbate 20 (trade name: Tween 20, etc.); and nonionic oil bath rinsing agents such as oxyethylated alkylphenol (trade name: Triton X100, etc.). Examples also include sodium deoxycholate; Zwittergents, i.e., synthetic Zwitter ionic detergents known as sulfobetaine, such as N-dodecyl-N,N-dimethyl-2-ammonio-1-ethanesulfonate and its homologues; and nonionic detergents such as octyl-$\beta$,D-glucopyranoside.

When using a surfactant, it is not added in a critical amount; for example, it may be used at ratios between about 0.001% and about 10%, preferably between about 0.01% and 3%.

Trialkyl phosphate treatment is especially valuable for the inactivation of envelope-coated viruses, such as hepatitis B virus, non-A non-B hepatitis virus, human immunodeficiency virus (HIV), Vesicular Stomatitis virus, Sindbis virus, etc. It is also possible to inactivate heat resistant viruses by heat treatment in a dry state for a sufficient time.

In the present invention, trialkyl phosphate treatment of the protein-containing composition is carried out at $-5°$ C. to 70° C., preferably 0° C. to 60° C. for more than 30 minutes, preferably 1 to 30 hours, more preferably 3 to 10 hours.

It is preferable that trialkyl phosphate treatment be carried out in the presence of a protease inhibitor to prevent protein activity reduction.

There is no particular limitation posed on the protease inhibitor as long as it is a substance which substantially inhibits protease activity. Examples of such substance include basic amino acids such as $\epsilon$-aminocaproic acid (EACA), lysine and arginine; and proteins such as aprotinin.

Usually, trialkyl phosphate is removed after trialkyl phosphate treatment. When using the surfactants and/or stabilizers, they are removed as well. Any method can be employed for this removal; examples include the method in which protein is adsorbed by affinity chromatography and the method in which protein is recovered by precipitation. A known method of heat treatment is also applicable.

Heat treatment of a dry composition may precede or follow trialkyl phosphate treatment, but it is preferable to carry it out after the trialkyl phosphate treatment. When heat treatment follows trialkyl phosphate treatment, the dry composition is obtained by removing trialkyl phosphate, etc., then recovering protein and lyophilizing it by a known method.

Heat treatment of the dry composition is carried out normally at 30° C. to 100° C., preferably 55° C. to 75° C. normally for 3 to 200 hours, preferably 10 to 100 hours. Heat treatment may be carried out in the presence of a stabilizer to protect the protein from heat. Examples of the stabilizer include sugar, sugar alcohol and amino acid.

A protein-containing composition in a dry form of the present invention does not substantially contain water and normal moisture content thereof is not more than 3%, preferably not more than 1%.

When a protein-containing composition is brought into contact with alkyl phosphate in the presence of a protease inhibitor according to the present invention, either liquid heat treatment or dry heat treatment can be employed. As in the dry heat treatment, liquid heat treatment is preferably conducted after trialkyl phosphate treatment. In that case, protein is recovered after the removal of trialkyl phosphate, etc.

When liquid heat treatment is employed, it is normally carried out at 30° C. to 100° C., preferably 55° C. to 75° C. normally for 1 to 100 hours, preferably 5–30 hours. Heat treatment may be carried out in the presence of a stabilizer to protect the protein from heat. Examples of the stabilizer include sugar, sugar alcohol and amino acid.

The production method of the present invention permits production of a protein-containing composition wherein viruses were efficiently inactivated without spoiling the protein activity.

Trialkyl phosphate treatment has a weak inactivating effect on viruses having no envelope. It should be noted, however, that the present invention permits significant inactivation of such viruses via a process wherein a dry protein-containing composition is subjected to heat treatment.

Also, in trialkyl phosphate treatment at 25° C. to 30° C., there is a possibility that proteolysis by coexisting protease in the solution may be promoted due to long residence at this temperature; however, protein activity reduction can be suppressed by conducting the treatment in the presence of a protease inhibitor.

Accordingly, the production method of the present invention is very favorable as an industrial production method for a pharmaceutically safer protein-containing composition, and it is especially valuable for the production of virus-inactivated protein preparations.

EXAMPLE 1

Production Method for a Composition Containing Blood Coagulation Factor VIII

Cryoprecipitate was dissolved in a 20 mM Tris-HCl buffer. To this solution was added aluminum hydroxide gel at 1% (v/v) to yield a deprothrombinized solution. To this solution were added TNBP [tri-(n-butyl) phosphate] and Tween 80 so that their final concentration became 0.3% (w/v) and 1% (w/v), respectively, and this was followed by virus inactivation treatment at 30° C. for 6 hours. Then, glycine was added so that its concentration became 2M, and this was followed by centrifugation to precipitate and remove fibrinogen. To the obtained supernatant was added sodium chloride so that its concentration became 1.5M, and this was followed by recovery of the factor VIII as a precipitate. The recovered factor VIII was dissolved in a 20 mM Tris-HCl buffer, and this was again followed by glycine fractionation and sodium chloride fractionation to remove the residual portions of TNBP and Tween 80. The factor VIII precipitate thus obtained was dissolved to a given concentration and then dispensed to vials and lyophilized. The lyophilized factor VIII preparation was subjected to dry heat treatment at 60° C. for more than 72 hours to yield a preparation which is safe against viruses.

EXAMPLE 2

Production Method for a Composition Containing Blood Coagulation Factor IX

DEAE-Sephadex was placed in blood plasma to adsorb the factor IX to the gel. After thoroughly washing the gel with a buffer containing 0.15M sodium chloride, the factor IX was eluted with a buffer containing 0.5M sodium chloride. To this eluate were added TNBP and Tween 80 so that their concentration became 0.3% (w/v) and 1%, respectively, and this was followed by virus inactivation treatment at 30° C. for more than 6 hours. DEAE-Sephadex was again placed in the virus-inactivated factor IX solution to adsorb the factor IX, and this was followed by gel washing, whereby TNBP and Tween 80 were removed into the washings. It is also possible to couple the factor IX to gel bound with an anti-factor-IX monoclonal antibody in place of DEAE-Sephadex and treat it in the same manner as above. After elution from the gel, the factor IX was adjusted to the desired ionic strength and titer, and then dispensed and lyophilized to yield a factor IX preparation. Further, dry heat treatment at 60° C. for more than 72 hours was conducted to inactivate the non-envelope viruses, whereby the preparation was made safer.

EXAMPLE 3

Production Method for a Thrombin-Containing Composition

Corn Fr II+III paste or Fr III paste was dissolved in a 0.15M sodium chloride solution. To this solution was added thromboplastin (placenta extract) to convert prothrombin to thrombin. Then, thrombin was adsorbed to SP-Sephadex. After thoroughly washing the gel with a 0.15M sodium chloride solution, thrombin was eluted with a buffer containing 0.5M sodium chloride. To this eluate were added 0.3% (w/v) TNBP and 1% (w/v) Tween 80, and this was followed by virus inactivation treatment at 30° C. for more than 6 hours. After virus inactivation treatment, thrombin was again adsorbed to SP-Sephadex or heparin-gel. After thoroughly washing the gel to remove TNBP and Tween 80, thrombin was eluted from the gel. The thrombin thus obtained was adjusted to the desired ionic strength and titer, and then dispensed and lyophilized, after which it was subjected to dry heat treatment at 60° C. for more than 72 hours.

EXAMPLE 4

Production Method for a Fibrinogen-Containing Composition

Corn Fr I paste was dissolved in a physiological saline solution. To this solution were added 0.3% (w/v) TNBP and 1% (w/v) Tween 80, and this was followed by virus inactivation treatment at 30° C. for more than 6 hours. Then, fibrinogen was precipitated by glycine-sodium chloride fractionation or ethanol fractionation. The fibrinogen precipitate thus obtained was dissolved in a physiological saline solution and then subjected to glycine-sodium chloride fractionation or ethanol fractionation to precipitate fibrinogen, which was then recovered. This fractionation procedure was conducted 3 to 5 times, during which TNBP and Tween 80 were removed into supernatants. The fibrinogen precipitate thus obtained was dissolved to a given concentration and then dispensed and lyophilized, after which it was subjected to dry heat treatment at 60° C. for more than 72 hours.

EXAMPLE 5

Production Method for a Composition Containing Blood Coagulation Factor VIII

Cryoprecipitate obtained by freeze-thawing normal human plasma, as the starting material, was extracted with, and dissolved in a 5-fold amount of 20 mM Tris-10 mM citrate buffer (pH 7.0). To this solution was added aluminum hydroxide gel in a ratio by volume of 1/10 relative to the amount of cryoprecipitate used, and this was followed by stirring for 30 minutes. Then, bentonite was added in a ratio of 6 g/l, and this was followed by stirring for 1 hour and then centrifugation at 4000 rpm for 30 minutes to yield a supernatant, which was then subjected to surfactant treatment for virus inactivation (after tri-n-butyl phosphate and Tween 80 were added so that their concentration became 0.3% and 1%, respectively, stirring was carried out at 30° C. for 6 hours) and then glycine fractionation. Glycine fractionation was achieved by glycine addition to the solution in a ratio of 150 g/l, stirring at 30° C. for 1 hour and subsequent centrifugation (4000 rpm, 30 minutes, 30° C.). To the supernatant thus obtained, sodium chloride was added (87 g/l), and this was followed by stirring for 1 hour to salt out the factor VIII fraction, whereby a centrifugal precipitation (4000 rpm, 30 minutes, 30° C.) was obtained.

Then, the salting-out precipitation was dissolved in a 20 mM Tris buffer (pH 7.0) and then adjusted to an adsorbance at 280 nm of 25 to 30 to yield a sample to be injected into the gel filtration column. The column packing used was Sephacryl S-400 HR, produced by Pharmacia. The sample injection volume was 5 to 7% relative to the column bed capacity. The factor VIII active fraction which had passed through the column was collected. The conditions of fractionation were as follows:

Injected sample: Salting-out precipitation solution
Column: Sephacryl S-400 HR
Solvent: 20 mM Tris-HCl, 10 mM $CaCl_2$, 1M NaCl buffer, pH 7.0

As a result, the blood coagulation factor VIII was eluted in the column void fraction, with impurity protein separated to high degree. The eluate was then adjusted to the desired ionic strength and titer, after which it was dispensed and lyophilized to yield a factor VIII preparation.

Further, dry heat treatment at 60° C. for more than 72 hours was conducted to make the preparation safer.

EXAMPLE 6

Corn Fr I paste was dissolved in a 0.055M sodium citrate buffer, pH 6.4, containing 0.025M EDTA-2Na and 10 units/ml aprotinin. This solution was heated at 50° C. for 30 minutes to denature and remove fibrinogen (Japanese Patent Application No. 4479/1982). This solution was concentrated. To the resulting concentrate were added 30 units/ml aprotinin, 0.3% (w/v) TNBP and 1% (w/v) Tween 80, and this was followed by virus inactivation treatment at 30° C. for more than 6 hours. After the virus inactivation treatment, fibronectin was adsorbed to DEAE-Sephadex. After thoroughly washing the gel to remove TNBP and Tween 80, fibronectin was eluted from the gel. This eluate was concentrated to yield a preparation which is safe against viruses.

EXAMPLE 7

The fibronectin obtained in Example 6 was adjusted to 30 mg/ml with a 0.05M Tris-phosphate buffer, pH 8.0. To 1 l of an aqueous solution thereof was added 1 kg of sucrose. After vigorous stirring, this solution was heated at 60° C. for 10 hours. After cooling, the solution was dialyzed against a 0.9% sodium chloride solution, and this was followed by centrifugation to yield a clear supernatant.

EXAMPLE 8

Cryoprecipitate was dissolved in a 20 mM Tris-HCl buffer. To this solution was added aluminum hydroxide gel at 1% (w/v) to yield a deprothrombinized solution. To this solution was added glycine so that its concentration became 2M to precipitate and remove fibrinogen. To the obtained supernatant was added sodium chloride so that its concentration became 1.5M, and this was followed by recovery of fibronectin into the supernatant. After desalting and concentration of this solution, 4% EACA (ε-aminocaproic acid) and then 0.3% (w/v) TNBP and 1% (w/v) Tween 80 were added to the concentrate, and this was followed by virus inactivation treatment at 30° C. for more than 6 hours. After virus inactivation treatment, the same procedure was followed as in Examples 6 and 7 to yield a preparation which is safe against viruses.

EXPERIMENT EXAMPLE 1

Virus Inactivation Effect

Examinations were made of the inactivation effect of the present invention on viruses present in compositions containing blood coagulation factor VIII, compositions containing blood coagulation factor IX, thrombin-containing compositions and fibrinogen-containing compositions.

METHOD OF EXPERIMENTATION

Samples of each preparation, namely, cryoprecipitate solutions for the factor VIII, DEAE-Sephadex eluates for the factor IX, SP-Sephadex eluates for thrombin and Fr.I paste solutions for fibrinogen were collected during production processes for respective preparations. To each sample was added TNBP and Tween 80 so that their concentration became 0.3% (w/v) and 1% (w/v), respectively, and this was followed by the addition of VSV or Sindbis virus, both are envelope viruses, and Echo virus, an envelopeless virus, as monitor virus, in a ratio of $10^6$ to $10^7$ virus particles/ml. Then, the sample was kept warmed at 30° C., and time-course sampling was conducted to determine the activity of residual viruses according to the method shown in Table 1. The results are given in Tables 2 through 4. In every preparation, VSV and Sindbis virus were inactivated below the detection limit by treatment at 30° C. for 1 hour. On the other hand, Echo virus, an envelopeless virus, was hardly inactivated even after 60 hours of treatment at 30° C.

TABLE 1

Test Virus, Host Cell Lines and Methods of Infection Level Determination

| Subject virus | Host cell line | Method of infection level determination |
|---|---|---|
| Vesicular stomatitis (Indiana strain) | FL | Plaque formation |
| Sindbis | CEF | Plaque formation |
| Echo (type 6) | HeLa | Observation of cell degenerating effect |

TABLE 2

Virus Inactivating Effect of TNBP/Tween 80 Treatment on Factor VIII

| Virus | TNBP/Tween 80 treatment | Duration (min.) of incubation at 30° C. | | | | | | | |
|---|---|---|---|---|---|---|---|---|---|
| | | 0 | 5 | 10 | 30 | 60 | 120 | 240 | 360 |
| VSV | TNBP/Tween 80 | $10^{6.2}$ | $10^{3.9}$ | $10^{3.0}$ | — | — | — | — | — |
| | control | $10^{6.6}$ | ND | $10^{6.5}$ | $10^{6.0}$ | $10^{6.2}$ | ND | $10^{5.9}$ | $10^{5.9}$ |
| Sindbis | TNBP/Tween 80 | $10^{7.0}$ | $10^{4.3}$ | $10^{3.9}$ | — | — | — | — | — |
| | control | $10^{6.7}$ | $10^{6.5}$ | $10^{6.7}$ | $10^{6.7}$ | $10^{6.6}$ | ND | $10^{6.6}$ | $10^{6.5}$ |
| Echo | TNBP/Tween 80 | $10^{6.7}$ | $10^{6.7}$ | ND | $10^{5.7}$ | $10^{5.5}$ | ND | $10^{4.5}$ | $10^{4.1}$ |
| | control | $10^{7.3}$ | $10^{6.7}$ | ND | $10^{6.3}$ | $10^{5.5}$ | ND | $10^{4.3}$ | $10^{4.3}$ |

Figures represent values of PFU/ml or TCID$_{50}$/ml;
— represents values less than $10^{2.7}$ PFU/ml;
control means no treatment with TNBP/Tween 80.

TABLE 3

Virus Inactivating Effect of TNBP/Tween 80 Treatment on Factor IX

| Virus | TNBP/Tween 80 treatment | Duration (min.) of incubation at 30° C. | | | | | | | |
|---|---|---|---|---|---|---|---|---|---|
| | | 0 | 5 | 10 | 30 | 60 | 120 | 240 | 360 |
| VSV | TNBP/Tween 80 | $10^{6.1}$ | — | — | — | — | — | — | — |
| | control | $10^{6.1}$ | $10^{5.8}$ | $10^{5.8}$ | $10^{5.7}$ | $10^{5.6}$ | ND | $10^{5.3}$ | $10^{5.8}$ |
| Sindbis | TNBP/Tween 80 | $10^{6.6}$ | $10^{4.3}$ | $10^{3.9}$ | $10^{2.9}$ | — | — | — | — |
| | control | $10^{6.7}$ | $10^{6.7}$ | $10^{6.7}$ | $10^{6.7}$ | $10^{6.7}$ | ND | $10^{6.7}$ | $10^{6.7}$ |
| Echo | TNBP/Tween 80 | $10^{6.9}$ | $10^{6.9}$ | ND | $10^{6.9}$ | $10^{6.7}$ | ND | $10^{6.9}$ | $10^{6.5}$ |

TABLE 3-continued

| Virus Inactivating Effect of TNBP/Tween 80 Treatment on Factor IX | | | | | | | | |
|---|---|---|---|---|---|---|---|---|
| | TNBP/Tween 80 | Duration (min.) of incubation at 30° C. | | | | | | |
| Virus | treatment | 0 | 5 | 10 | 30 | 60 | 120 | 240 | 360 |
| | control | $10^{6.7}$ | ND | ND | $10^{6.7}$ | $10^{6.9}$ | ND | ND | $10^{6.5}$ |

Figures represent values of PFU/ml or TCID$_{50}$/ml;
— represents values less than $10^{2.7}$ PFU/ml;
control means no treatment with TNBP/Tween 80.

TABLE 4

| Virus Inactivating Effect of TNBP/Tween 80 Treatment on Fibrinogen | | | | | | | | |
|---|---|---|---|---|---|---|---|---|
| | TNBP/Tween 80 | Duration (min.) of incubation at 30° C. | | | | | | |
| Virus | treatment | 0 | 5 | 10 | 30 | 60 | 120 | 240 | 360 |
| VSV | TNBP/Tween 80 | $10^{5.8}$ | — | — | — | — | — | — | — |
| | control | $10^{5.7}$ | $10^{5.9}$ | $10^{5.9}$ | $10^{6.0}$ | $10^{5.3}$ | ND | $10^{4.7}$ | $10^{5.2}$ |
| Sindbis | TNBP/Tween 80 | $10^{7.0}$ | $10^{4.0}$ | — | — | — | — | — | — |
| | control | $10^{7.0}$ | $10^{7.1}$ | $10^{7.0}$ | $10^{7.2}$ | $10^{7.0}$ | ND | $10^{7.0}$ | $10^{6.8}$ |
| Echo | TNBP/Tween 80 | $10^{6.5}$ | $10^{6.1}$ | ND | $10^{5.9}$ | ND | $10^{4.9}$ | $10^{4.3}$ | $10^{4.1}$ |
| | control | $10^{6.5}$ | ND | ND | $10^{6.1}$ | ND | $10^{5.1}$ | ND | $10^{4.1}$ |

Figures represent values of PFU/ml or TCID$_{50}$/ml;
— represents values less than $10^{2.7}$ PFU/ml;
control means no treatment with TNBP/Tween 80.

EXPERIMENT EXAMPLE 2

Stability of Protein

In the case of the factor VIII, 0.3% (w/v) TNBP and 1% (w/v) Tween 80 were added to a cryopaste extract, and this extract was kept warmed at 30° C. Time-course sampling was conducted to determine factor VIII activity. Based on the finding that the 24-hr residual activity was 80% (see FIG. 1), it was judged that the factor VIII activity was hardly lost due to treatment at 30° C. for 6 hours. Thus, stabilizer screening was not conducted. As for stability to dry heating, more than 95% activity was maintained even after 72 hours of treatment at 60° C.; stabilizer screening was not conducted as well.

Figure 2:
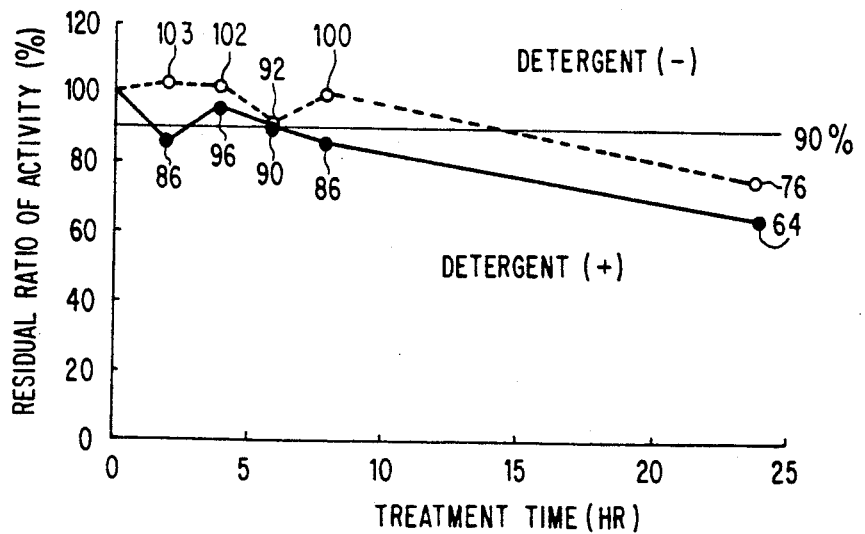
FIG. 2 shows time courses of the influence of surfactant treatment on the residual activity ratio of blood coagulation factor IX: -○- represents data obtained in the absence of a surfactant; -●- represents data obtained in the presence of a surfactant.

In the case of the factor IX, 0.3% (w/v) TNBP and 1% (w/v) Tween 80 were added to a DEAE eluate, and this eluate was kept warmed at 30° C. Time-course sampling was conducted to determine factor IX activity. Although slight activity reduction occurred after 24 hours, i.e., the 24-hr residual activity ratio was 76%, almost no significant reduction occurred after 6 hours of treatment at 30° C. Thus, no stabilizer was added. (see FIG. 2).

As for stability to dry heating, more than 95% activity was maintained even after 72 hours of treatment at 60° C.; stabilizer screening was not conducted as well.

Figure 3:
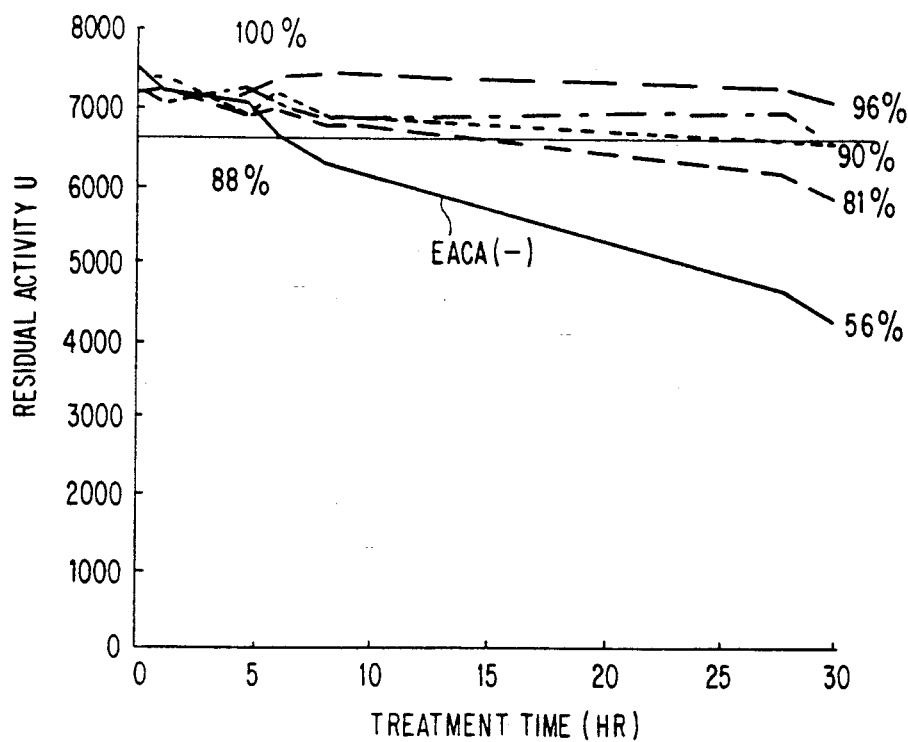
FIG. 3 shows time courses of the influence of EACA addition on the residual activity ratio of thrombin in surfactant treatment:—represents data obtained in the absence of EACA;-represents data obtained in the presence of 1% EACA; ... represents data obtained in the presence of 2% EACA;-represents data obtained in the presence of 4% EACA;—represents data obtained in the presence of 8% EACA.
Figure 4:
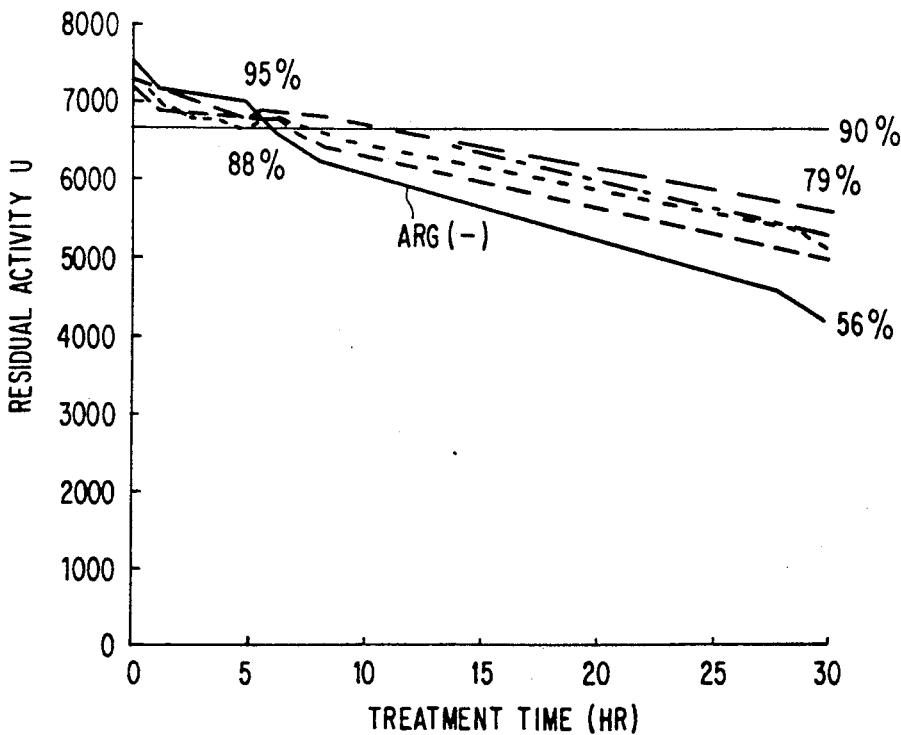
FIG. 4 shows time courses of the influence of arginin addition on the residual activity ratio of thrombin in surfactant treatment:—represents data obtained in the absence of arginin;-represents data obtained in the presence of 1% arginin ... represents data obtained in the presence of 2% arginin;-represents data obtained in the presence of 4% arginin;—represents data obtained in the presence of 8% arginin.

In the case of thrombin, 0.3% (w/v) TNBP and 1% (w/v) Tween 80 were added to an SP-Sephadex eluate, and this eluate was kept warmed at 30° C. Time-course sampling was conducted to determine thrombin activity. Significant activity loss occurred after 30 hours, and it was judged that 90% activity was difficult to be maintained even after 6 hours of treatment at 30° C. Thus, stabilizer screening was conducted. As a result, thrombin activity reduction was successfully suppressed by the addition of EACA (ε-aminocaproic acid) or arginin. In particular, when EACA was added at a concentration above 2%, more than 90% activity was maintained even after 30 hours of treatment at 30° C. (see FIGS. 3 and 4).

Figure 5:
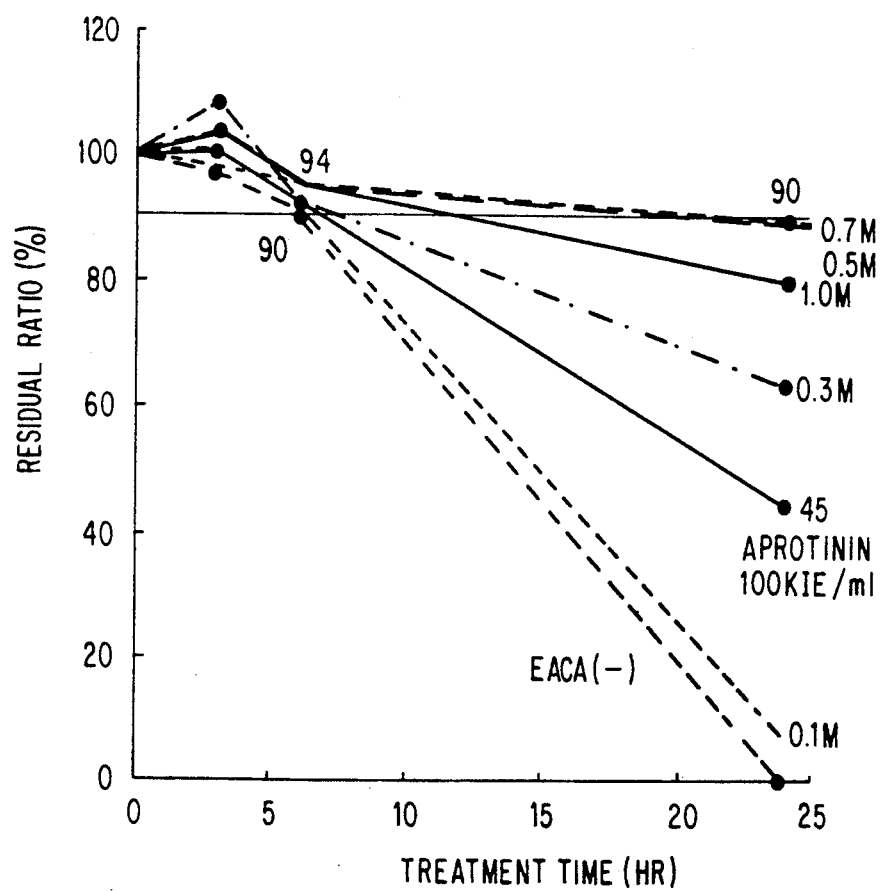
FIG. 5 shows time courses of the influence of EACA addition on the residual activity ratio of fibrinogen in surfactant treatment.

In the case of fibrinogen, 0.3% (w/v) TNBP and 1% (w/v) Tween 80 were added to an Fr.I paste solution, and this solution was kept warmed at 30° C. Time-course sampling was conducted to determine fibrinogen coagulation activity. It was found that there was no coagulation activity after 24 hours of treatment at 30° C.; stabilizer screening was conducted. Aprotinin and EACA were both found to have a stabilizing effect. When EACA was added at a concentration above 5%, more than 90% coagulation activity was maintained even after 24 hours of treatment at 30° C. (see FIG. 5).

EXPERIMENT EXAMPLE 3

To the desalted concentrate obtained in Example 8, 0.3% (w/v) TNBP and 1% (w/v) Tween 80 were added, and this concentrate was kept warmed at 30° C. The gelatin binding activity of fibronectin was determined after 3, 6 and 30 hours; 6-hrs residual activity ratio was 85% and it decreased to 55% after 30 hours. Thus, stabilizer screening was conducted. When EACA was added at a concentration above 2% or aprotinin was added at a concentration above 10 units/ml, fibronectin activity reduction was successfully suppressed (see Tables 5 and 6).

TABLE 5

| Amount of EACA added (%) | Residual gelatin binding activity ratio (%)[1] |
|---|---|
| Not added | 55 |
| 1 | 84 |
| 2 | 92 |
| 4 | 96 |

Note
[1]Figures are shown in values relative to the value before the treatment taken as 100%.

TABLE 6

| Amount of aprotinin added (unit/ml) | Residual gelatin binding activity ratio (%)[1] |
|---|---|
| Not added | 55 |
| 10 | 91 |
| 30 | 97 |
| 50 | 98 |

Note
[1]Figures are shown in values relative to the value before the treatment taken as 100%.

EXPERIMENT EXAMPLE 4

To the desalted concentrate obtained in Example 8 were added 30 units/ml aprotinin and then 0.3% (w/v) TNBP and 1% (w/v) Tween 80. To this mixture were added VSV or Sindbis virus, both are envelope viruses, and Echo virus, an envelopeless virus, as monitor virus, in a ratio of $10^6$ to $10^7$ virus particles/ml. Then, the mixture was kept warmed at 30° C. and time-course sampling was conducted to determine the activity of residual viruses according to the method shown in Table 7. The results are given in Table 8. In every preparation, VSV and Sindbis virus were inactivated to below the detection limit by treatment at 30° C. for 30 hours. On the other hand, Echo virus, an envelopeless virus, was hardly inactivated even after 6 hours of treatment at 30° C.

TABLE 7

Test Virus, Host Cell Lines and Methods of Infection Level Determination

| Subject virus | Host cell line | Method of infection level determination |
|---|---|---|
| Vesicular stomatitis (Indiana strain) | FL | Plaque formation |
| Sindbis | CEF | Plaque formation |
| Echo (type 6) | HeLa | Observation of cell degenerating effect |

TABLE 8

Virus Inactivating Effect of TNBP/Tween 80 Treatment on Fibrinogen

| Virus | TNBP/Tween 80 treatment | Duration (min.) of incubation at 30° C. | | | | | | | |
|---|---|---|---|---|---|---|---|---|---|
| | | 0 | 5 | 10 | 30 | 60 | 120 | 240 | 360 |
| VSV | TNBP/Tween 80 | $10^{6.8}$ | $10^{4.0}$ | $10^{2.9}$ | — | — | — | — | — |
| | control | $10^{6.5}$ | $10^{6.3}$ | $10^{6.3}$ | $10^{6.1}$ | $10^{6.1}$ | ND | $10^{6.0}$ | $10^{6.0}$ |
| Sindbis | TNBP/Tween 80 | $10^{6.1}$ | $10^{4.5}$ | $10^{3.8}$ | — | — | — | — | — |
| | control | $10^{6.4}$ | $10^{6.6}$ | $10^{6.7}$ | $10^{6.4}$ | $10^{6.4}$ | ND | $10^{6.4}$ | $10^{6.3}$ |
| Echo | TNBP/Tween 80 | $10^{6.7}$ | $10^{6.5}$ | ND | $10^{5.4}$ | $10^{5.2}$ | ND | $10^{4.1}$ | $10^{3.7}$ |
| | control | $10^{7.0}$ | $10^{6.7}$ | ND | $10^{6.1}$ | $10^{5.3}$ | ND | $10^{4.4}$ | $10^{3.9}$ |

Figures represent values of PFU/ml or $TCID_{50}$/ml;
— represents values less than $10^{2.7}$ PFU/ml;
control means no treatment with TNBP/Tween 80.

We claim:

1. A method for preparing a virus-inactivated protein-containing composition from a protein-containing composition which may be contaminated with virus and which composition is treated in a liquid state and in a dry state, comprising the steps of (a) contacting the protein-containing composition in a liquid state with a trialkyl phosphate, and (b) heat-treating the protein-containing composition in a dry state to the extent that a non-envelope virus contained therein is inactivated, wherein the steps (a) and (b) are performed in any order.

2. A method as in claim (1), wherein the protein is derived from plasma.

3. A method as in claim (1), wherein the heat-treating step (b) follows contacting step (a).

4. A method as in claim (1), wherein the trialkyl phosphate is tri-(n-butyl) phosphate.

5. A method as in claim (1), wherein a trialkyl phosphate is used in an amount of from 0.01 to 10 (w/v) %.

6. A method as in claim (1), wherein the protein-containing liquid composition is brought into contact with a trialkyl phosphate in the presence of a surfactant.

7. A method as in claim (1), wherein the heat treatment is conducted at 30° C. to 100° C. for 3 to 200 hours.

8. A method as in claim (1), wherein the protein is at least one species selected from among the group consisting of blood coagulation factor VIII, blood coagulation factor IX, thrombin, fibrinogen and fibronectin.

9. A method for preparing a virus-inactivated protein-containing composition from a protein-containing composition which may be contaminated with virus, comprising the steps of:
   (a) contacting a protein-containing liquid composition with a trialkyl phosphate;
   (b) removing the trialkyl phosphate and recovering the protein from the thus treated protein-containing liquid composition;
   (c) lyophilizing the recovered protein to obtain a dry protein-containing composition; and
   (d) heat-treating the dry protein-containing composition to the extent that a non-envelope virus contained therein is inactivated.

10. A method as in claim 1, wherein said virus is echo virus.

11. A method as in claim 9, wherein said virus is echo virus.

12. A method for preparing a virus-inactivated protein-containing composition from a protein-containing composition which may be contaminated with virus, comprising the steps of:
   (a) contacting a protein-containing liquid composition with a trialkyl phosphate;
   (b) removing the trialkyl phosphate and recovering the protein from the thus treated protein-containing liquid composition;
   (c) lyophilizing the recovered protein to obtain a dry protein-containing composition; and
   (d) heat-treating the dry protein-containing composition to the extent that a non-envelope virus contained therein is inactivated, wherein the protein is at least one species selected from the group consisting of blood coagulation factor VIII, blood coagulation factor IX, thrombin and fibrinogen.

13. A method as in claim 12, wherein said virus is echo virus.

14. A method as in claim 12, wherein the trialkyl phosphate treatment is carried out at from −5° C. to 70° C. for more than 30 minutes.

15. A method as in claim 12, wherein the heat treatment is conducted at 30° C. to 100° C. for 3 to 200 hours.

16. A method as in claim 12, wherein the heat treatment is conducted at 55° C. to 75° C. for 10 to 100 hours.

* * * * *